US012290689B2

(12) United States Patent
Efimov et al.

(10) Patent No.: US 12,290,689 B2
(45) Date of Patent: May 6, 2025

(54) SYSTEMS AND METHODS FOR SELECTIVE HIS BUNDLE MAPPING AND PACING

(71) Applicants: The George Washington University, Washington, DC (US); Northwestern University, Evanston, IL (US)

(72) Inventors: Igor R. Efimov, Arlington, VA (US); Jaclyn Ann Brennan, Fairfax, VA (US); John A. Rogers, Evanston, IL (US)

(73) Assignees: The George Washing University, Washington, DC (US); Northwestern University, Evanston, IL (US)

( * ) Notice: Subject to any disclaimer, the term of this patent is extended or adjusted under 35 U.S.C. 154(b) by 331 days.

(21) Appl. No.: 17/579,218

(22) Filed: Jan. 19, 2022

(65) Prior Publication Data
US 2022/0226651 A1 Jul. 21, 2022

Related U.S. Application Data

(60) Provisional application No. 63/139,178, filed on Jan. 19, 2021.

(51) Int. Cl.
*A61N 1/362* (2006.01)
*A61B 18/14* (2006.01)
(Continued)

(52) U.S. Cl.
CPC ........ *A61N 1/3627* (2013.01); *A61B 18/1492* (2013.01); *A61M 25/1002* (2013.01);
(Continued)

(58) Field of Classification Search
CPC ............... A61N 1/3627; A61N 1/3684; A61B 18/1492; A61M 25/1002; A61M 2025/1043
See application file for complete search history.

(56) References Cited

U.S. PATENT DOCUMENTS

| | | | |
|---|---|---|---|
| 2008/0058656 A1* | 3/2008 | Costello | A61B 5/1107 600/595 |
| 2010/0249865 A1* | 9/2010 | Zhang | A61B 5/14535 607/17 |
| 2018/0235692 A1* | 8/2018 | Efimov | A61B 5/0538 |

FOREIGN PATENT DOCUMENTS

WO  2022040292 A1  2/2022

OTHER PUBLICATIONS

Andrew J.M. Lewis et al., "His Bundle Pacing: A New Strategy for Physiological Ventricular Activation," Journal of he American Heart Association, DOI: 10.1161/JAHA. 118.010972, (c) 2019, 9 pages.
(Continued)

*Primary Examiner* — Mallika D Fairchild
*Assistant Examiner* — Thien Jason Tran
(74) *Attorney, Agent, or Firm* — Blank Rome LLP

(57) ABSTRACT

Systems and methods are disclosed for an electrical sensing, pacing, and ablation device comprising a bendable and stretchable balloon catheter and a bendable and stretchable first layer connected to or embedded in said balloon catheter, where the first layer has an electrode array with a plurality of electrodes. The is also a bendable and stretchable second layer connected to or embedded in the balloon catheter, and the second layer has a pressure sensor array with a plurality of pressure sensors.

22 Claims, 16 Drawing Sheets

(51) Int. Cl.
 *A61M 25/10* (2013.01)
 *A61N 1/368* (2006.01)
 *A61B 18/00* (2006.01)
(52) U.S. Cl.
 CPC .... *A61N 1/3684* (2013.01); *A61B 2018/0022* (2013.01); *A61B 2018/00351* (2013.01); *A61B 2018/00577* (2013.01); *A61M 2025/1043* (2013.01)

(56) References Cited

OTHER PUBLICATIONS

Mengdi Han, et al., "Catheter-integrated soft multilayer electronic arrays for multiplexed sensing and actuation during cardiac surgery," Nature Biomedical Engineering, vol. 4, Oct. 2020, pp. 997-1009.

* cited by examiner

SYSTEMS AND METHODS FOR SELECTIVE HIS BUNDLE MAPPING AND PACING

CROSS-REFERENCE TO RELATED APPLICATIONS

This application claims the benefit of U.S. Provisional App. No. 63/139,178, filed Jan. 19, 2021, the entire contents of which are incorporated herein by reference.

STATEMENT REGARDING FEDERALLY FUNDED RESEARCH

This invention was made with government support under Grant Nos. 3OT2OD023848 and R01HL141470 from the National Institutes of Health. The government has certain rights in the invention.

FIELD OF THE INVENTION

The present invention is directed to devices and methods for electrically sensing, mapping, and pacing mammalian tissue, more specifically, cardiac tissue.

BACKGROUND OF THE INVENTION

Cardiac resynchronization therapy (CRT) is a widely used, effective treatment modality for patients with symptomatic drug-refractory heart failure, but 30-40% of those treated do not respond favorably. CRT attempts to improve symptoms and mortality of electrical dyssynchrony with an implantable bi-ventricular pacing device to directly pace the right and left ventricular myocardium and restore electrical synchronization. However, this technique can be ineffective for certain patients due to scar burden, suboptimal lead positioning, variable etiologies of heart failure, and patterns of electro-mechanical dyssynchrony. His bundle pacing (HBP) is considered to be a more physiological approach for CRT because of its ability to overcome limitations of biventricular pacing by directly activating the intrinsic electro-mechanical sequence of the heart via electrical excitation of the conduction system of the heart comprised of the bundle of His, left and right bundle branches, and the Purkinje network. A number of studies have proven the feasibility of HBP for atrioventricular (AV) node ablation and AV block, but this technology is still in its infancy for CRT. Currently, major obstacles for adopting HBP for CRT include limitations in our biological understanding of His bundle conduction as well the difficulty in accurately sensing and selectively pacing the His bundle.

To address those and other deficiencies in the art, state-of-the-art engineering tools are applied herein to develop a novel conformal bioelectronic catheter to precisely map and achieve selective HBP (s-HBP) in which electrical activation will occur directly over the His-Purkinje system. The human atrioventricular (AV) junction (including the nearby regions of atrial and ventricular septum, atrioventricular (AV) node, and the His bundle) are mapped by conformal pacing-mapping system. The feasibility of the system is supported by previous work in our lab on AV junction pacing and optical mapping, 3D anatomical reconstruction, and pacing, as well the application of multi modal, multi layered soft organ conformal bioelectronics for cardiac mapping, stimulation, and ablation. It is believed that with an improved understanding of human His bundle conduction as well as the novel capabilities of technologically advanced organ conformal bioelectronics, one can improve s-HBP with minimally invasive and precise techniques.

SUMMARY OF THE INVENTION

The present technology involves several aspects that incorporate improvements over preexisting devices. Exemplarily, the technology includes a conformal bioelectronic device for high resolution mapping of AV node conduction pathways, a conformal bioelectronics device for selectively pacing AV node conduction pathways, and a conformal bioelectronic device with concurrent pressure, temperature, and electrical sensing capabilities for Selective His bundle pacing without active fixation. The present technology also includes a minimally invasive and removable flexible and stretchable catheter device for AV node conduction pathway mapping and pacing with the ability to identify the minimum pacing threshold for capturing select regions of the AV node conduction pathway (unique to each heart). In certain embodiments, the device also has the precise ability to locate optimal pacing sites (unique to each heart).

In certain embodiments, the technology comprises an electrical sensing and pacing device comprising a bendable and stretchable balloon catheter and a bendable and stretchable first layer connected to or embedded in said balloon catheter, where first layer has an electrode array with a plurality of electrodes. There is also a bendable and stretchable second layer connected to or embedded in the balloon catheter, and the second layer has a pressure sensor array with a plurality of pressure sensors. There is also a bendable and stretchable optional third layer connected to or embedded in the balloon catheter, and the third layer has a temperature sensor array with a plurality of temperature sensors.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
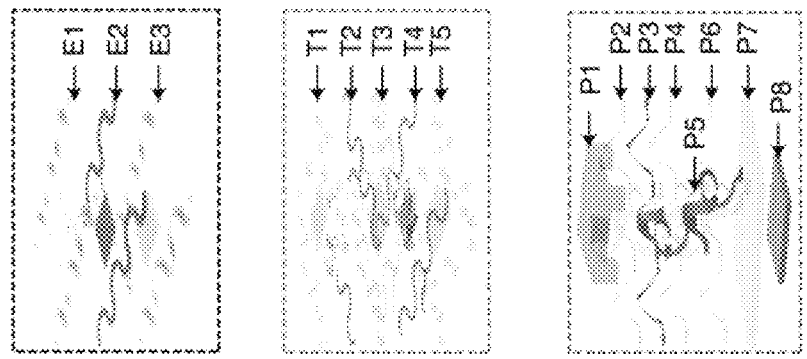
FIG. 1A is a diagram showing exemplary presents a schematic illustration of the device arrays in a multilayer format of the electrical sensing and pacing device in accordance with one embodiment of the disclosure.
Figure 1A:
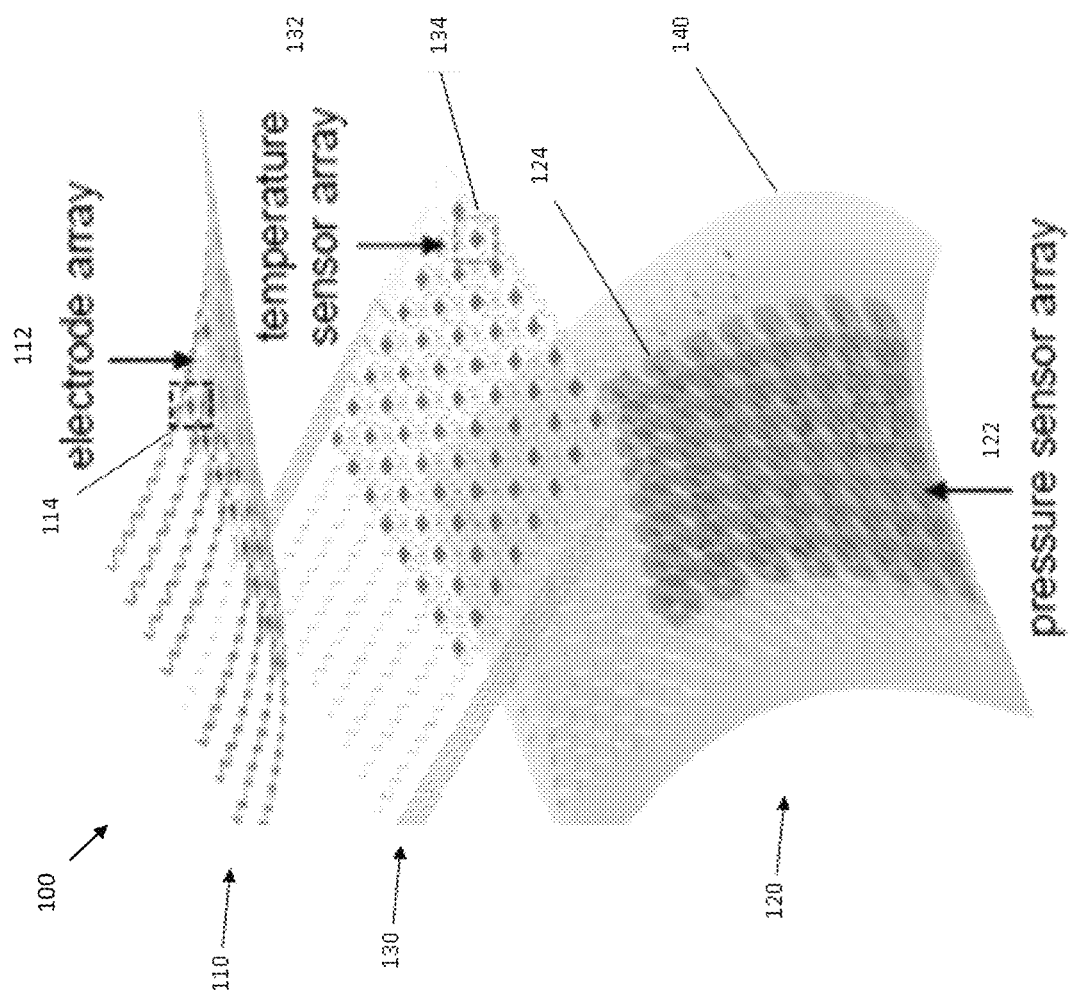

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes, it being understood that the invention may be embodied in other forms not specifically shown in the drawings.

Implantable cardiac pacemakers are currently the only definitive therapy for nonreversible bradyarrhythmias or symptomatic drug-refractory heart failure, and the need for these devices only continues to grow as the population ages. Standard cardiac pacemaking devices pace the right ventricular (RV) apex to activate myocardial tissue and improve the diastolic filling pattern. However, there is continuous debate on the effectiveness, as pacing the RV alone can cause electromechanical dyssynchrony, progressive left ventricular (LV) systolic dysfunction, and even an increased risk of heart failure. Additionally, RV pacing is not always a viable option for patients, as it has been shown to be deleterious in cases when AV node ablation is required. AV node ablation is a common procedure in the treatment of AF and chronic and recurrent AV node reentrant tachycardia (AVNRT), a disease which predominantly presents in women and is the most common form of supraventricular tachycardia. With AV node ablation, the electrical connection between the atria and ventricles is physically severed, and the heart requires an implantable cardiac pacemaker to restore proper electromechanical function. However, chronic RV pacing after AV node ablation can induce ventricular dyssynchrony in almost 50% of patients with atrial fibrillation (AF), so alternative more synchronous pacing options are imperative.

Due to the myriad problems with RV pacing of the heart, biventricular cardiac pacemaking—also known as cardiac resynchronization therapy (CRT)—has become an attractive alternative. Introduced in the 1990s, CRT is now a widely-used, effective treatment modality for patients with mild to severe systolic heart failure with abnormal QRS duration and morphology. It attempts to improve symptoms and mortality of electromechanical dyssynchrony events by employing a bi-ventricular pacing device to directly engage the ventricular muscle of both ventricles and thus restore electrical resynchronization. Though a revolutionary alternative to RV pacing, CRT has been found to be ineffective for approximately 30-40% of patients with persistent symptoms of systolic heart failure. The etiology of CRT impotence is an area of active investigation, though certain factors which are assumed to play a role include patient scar burden, improper lead positioning, inconsistent pacing, and variable etiologies of heart failure.

To offset the continuing complications of RV pacing and CRT, recent attention has turned away from direct pacing of the myocardium and has instead focused on reactivating the cardiac conduction system. Principally, this would more favorably mimic the true physiological activation of the heart. Since the function of hearts His bundle is to transmit electrical signals from the AV node to the endocardium of both ventricles through its left and right bundle branches and Purkinje fibers, direct activation of the His bundle could more effectively mimic the true physiological conduction sequence in the ventricles and thus would produce a more synchronous mechanical contraction. A number of studies have already validated HBP in scenarios of both AV node ablation and AV block. In the 2000 pioneering clinical study of permanent HBP in AF patients undergoing AV node ablation, HBP was met with over a 70% success rate after the AV node was ablated. More recent AV node ablation studies have achieved even higher HBP success rates of 81% with resultant improvements in LV diastolic dimensions and LV ejection fraction, and up to 84% in patients with advanced AV block. Taken together, HBP holds significant promise as both an attractive and effective alternative pacing modality to RV pacing or CRT for the many patients who so heavily rely on permanent implantable pacemakers.

Though several studies have proven the feasibility of HBP, this technology is still in its infancy. Currently, the two major obstacles facing widespread adoption of HBP include (1) limitations in our biological understanding of His bundle conduction properties including longitudinal dissociation and (2) the difficulty in accurately sensing and selectively pacing the His bundle due its niche anatomic location below the surface of endocardium.

First, a detailed understanding of the anatomy of the His bundle and its proximal bundle branches is crucial for understanding various conduction disorders as well as approaches for permanent HBP. After its first anatomical discovery in 1883 by Wilhelm His Jr, the His bundle was analyzed for its physiological attributes by Sunao Tawara in 1903. Tawara surmised that the His bundle was an anatomical continuation of the AV node which provided the connection of electrical signals to the left and right bundle branches. Then, in 1919, Kaufman and Rothberger proposed the theory of "functional longitudinal dissociation" in the His bundle, which suggested that conduction fibers arose from distinct pathways of the AV node and which were predestined to the individual bundle branches. In 1977, Narula clinically confirmed this longitudinal dissociation of the His bundle, showing that left bundle branch block (LBBB) can be corrected with HBP. Just one year later, El-Sherif et al. followed up on the other side of this work and found that patients with right bundle branch block (RBBB) also resulted in normalization of the QRS complex with HBP. Taken together, these studies indicate that the His bundle possesses two unique pathways of electrical conduction into the ventricular myocardium which are divided somewhere within the structure of the His bundle itself, and that HBP can shorten QRS intervals. However, it is unclear where and how these pathways are split within the His bundle this relatively limited understanding of these pathways makes it difficult to reasonably understand the pros and cons of "selective" (s-HBP) and "non-selective" (ns-HBP) pacing.

Second, placement of the leads in permanent HBP can be technically challenging due to the His bundles subendocardial location within a 1 cm$^2$ area of the atrial and ventricular septum. Device implantation of permanent HBP currently relies on screws, but this technology could damage the His bundle and surrounding myocardium and precludes follow-up or alterations in the pacing site location post implantation. Just as the traditional cardiac pacemaking market is seeing progressive improvements in device size and implantation methods for longer term and less-invasive pacing (e.g. leadless pacing systems), there is hope that technological advancements can similarly deliver more optimal delivery tools for effective and flexible pacing of the His bundle.

The current technology aims to overcome the current limitations of clinical HBP by (1) expanding our scientific understanding of the human His bundles molecular biology and anatomic structure, conduction pathways of longitudinal dissociation, and excitability, and (2) creating a novel, miniature conformal bioelectronic catheter for precision pace-mapping and guidance of implantation of effective HBP lead in the clinical settings.

Disclosed herein, for the first time, are systems and methods to functionally, molecularly, and anatomically characterize the normal and arrhythmic conduction pathways of the His bundle in the human heart using dual-sided optical and electrical mapping and anatomical RNAseq; (1) it will mechanistically investigate the important and clinically relevant concept of longitudinal dissociation in the human heart via combined functional studies and 3D anatomical reconstructions; and (2) it will create and apply a novel, multimodal, multilayered soft conformal bioelectronic catheter with advanced multilayered network of sensors and actuators for minimally invasive and adjustable in vivo electrophysiological study of the human heart conduction system and guiding implantation of a permanent s-HBP lead.

Hardware Design

In one embodiment of the technology, multifunctional collections of sensors, actuators and associated electronics are mounted on elastic surfaces in multilayer designs in which each layer serves a distinct function. Stretchable interconnects made from gold (Au). In certain exemplary embodiments, the interconnects may be 100 to 300 nm in thickness and 15 to 50 µm in width, sandwiched in polyimide (PI), which is 1 to 3.3 µm in thickness and 21 to 100 µm in width, creating multiplexed arrays covering areas of ~1 cm×1 cm. One of ordinary skill in the art will readily recognize that the interconnects may have other medically acceptable dimensions and may use other materials that perform analogous functionalities. The network demonstrated here includes electrodes (8×8) for electrophysiological recording and electrical stimulation (that is, for radiofrequency ablation, RFA, and/or irreversible electroporation, IRE), temperature sensors (8×8) for precision thermography and pressure sensors (8×8) for measuring the forces associated with soft-tissue contact, corresponding collectively to capabilities in multifunctional spatiotemporal mapping.

FIG. 1A presents a schematic illustration of the device arrays in a multilayer format of the electrical sensing device 100 in accordance with one embodiment of the disclosure. As shown, the electrical sensing device 100 includes a first layer 110, second layer 120, and an optional third layer 130. In the example embodiment shown, the first layer 110 is an electrode array 112 having a plurality of electrodes 114 interconnected with one another and arranged in rows and/or columns. The second layer 120 is a pressure sensor array 122 having a plurality of pressure sensors 124 interconnected with one another and arranged in rows and/or columns. The pressure sensor 124 can be a strain sensor having a bent section. As the bent section deforms, the resistance of the strain sensor changes. The third layer 130 can optionally be provided that in one embodiment includes a temperature sensor array 132 having a plurality of temperature sensors 134 interconnected with one another and arranged in rows and/or columns.

The top functional system allows electrophysiological mapping and RFA or IRE, with layers E1 (the top polymer film with openings), E2 (the array of electrodes and interconnects) and E3 (the bottom polymer film) for the electrode array. The next system enables measurements of temperature distributions, with layers T1 (the top polymer), T2 (the array of temperature sensors and row selection lines), T3 (a polymer interlayer with via openings), T4 (the column selection lines) and T5 (the bottom polymer film). The bottom system supports measurements of pressure distributions, with layers P1 (the array of silicon cavities), P2 (the top polymer film), P3 (the array of pressure sensors and row selection lines), P4 (a polymer interlayer with via openings), P5 (the column selection lines), P6 (the bottom polymer film), P7 (a layer of silicone elastomer) and P8 (an array of rigid islands).

In addition, the electrical sensing device 100 can include a flexible (e.g., bendable) and stretchable substrate 140 having a first side with a first surface and a second side opposite the first side with a second surface opposite the first surface. The first and second layers 110, 120 can be connected at the first and/or second surfaces or can be embedded or partially embedded at the first and/or second sides. The device 100, including each layer 110, 120, 130 and the substrate 140, is flexible and stretchable. As shown in FIGS. 1G and 1H, in one embodiment the substrate 140 can be a balloon that is deflated for insertion into the patient, then inflated once inserted to a desired position. FIG. 1G is an image of the array of electrodes transferred onto a balloon catheter of silicone, shown in a deflated and inflated configuration, while FIG. 1H is an image of the array of temperature sensors transferred on a balloon catheter of polyurethane, shown in a deflated and inflated configuration.

Figure 1B:
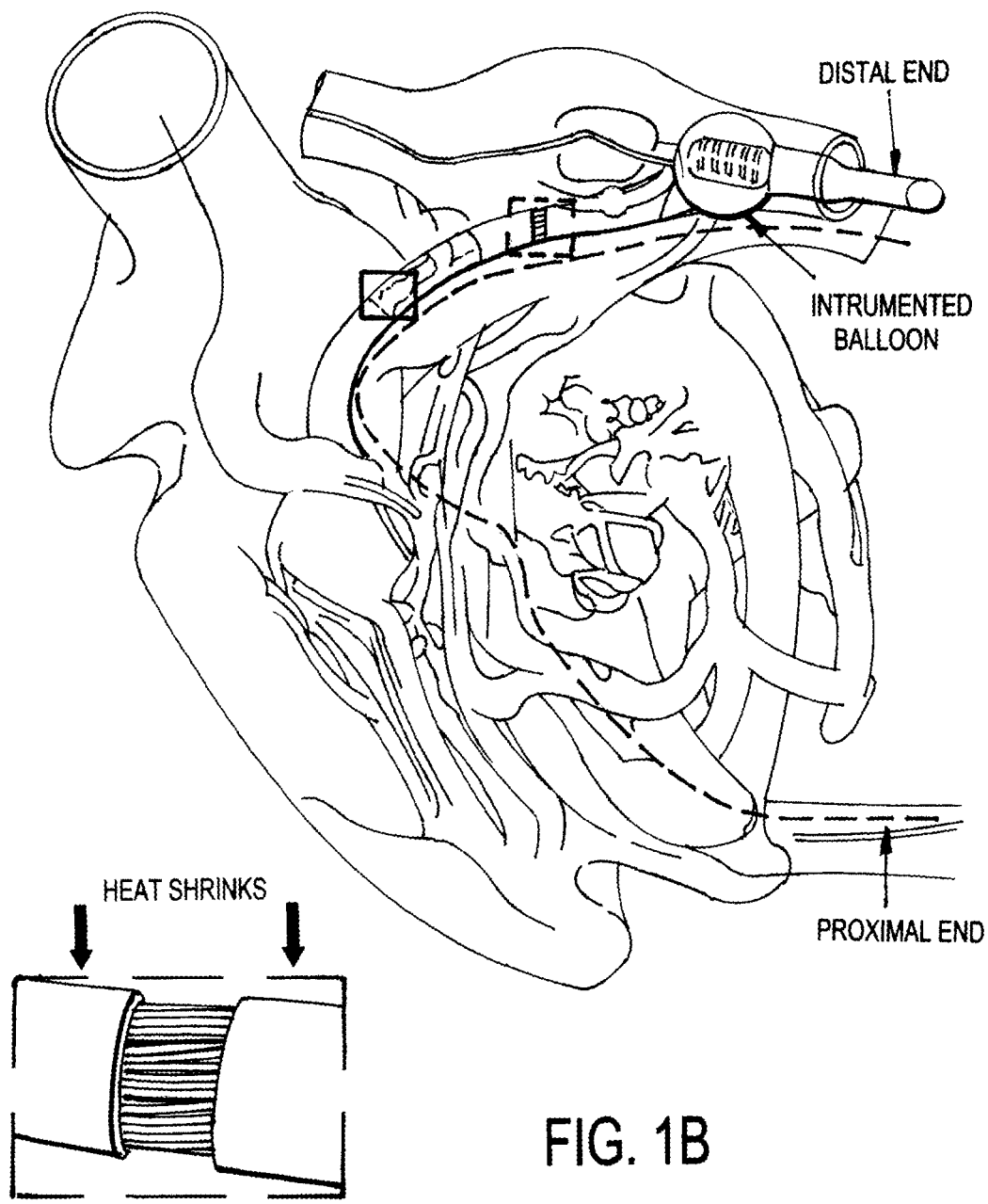
FIG. 1B is an image of an inflated, instrumented balloon catheter inserted into a transparent heart model, where the green dashed curve illustrates the path of the catheter. Scale bars, 1 cm (main image); 2 mm (inset).
Figure 1C:
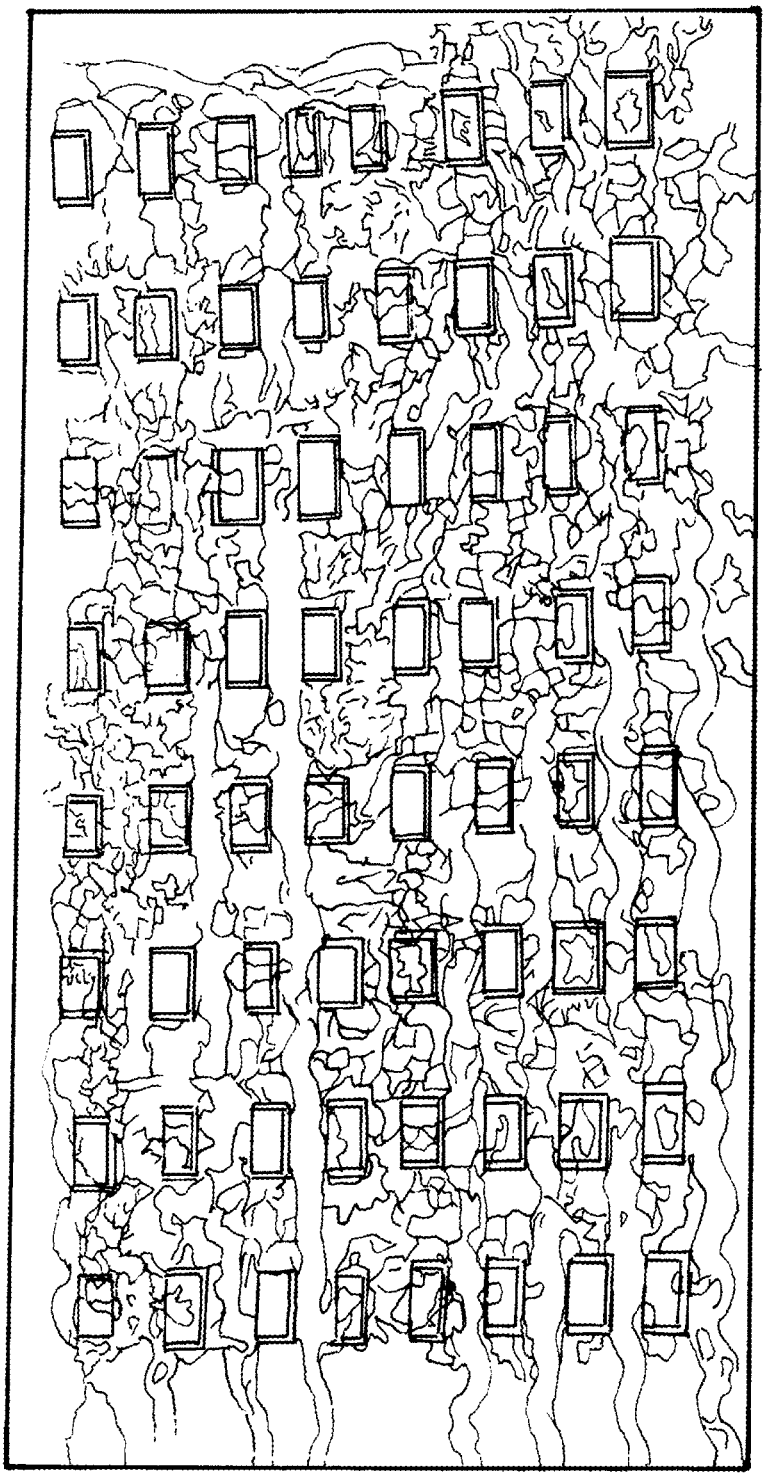
FIG. 1C is an image of the vertically stacked arrays of electrodes, temperature sensors and pressure sensors.
Figure 1D:
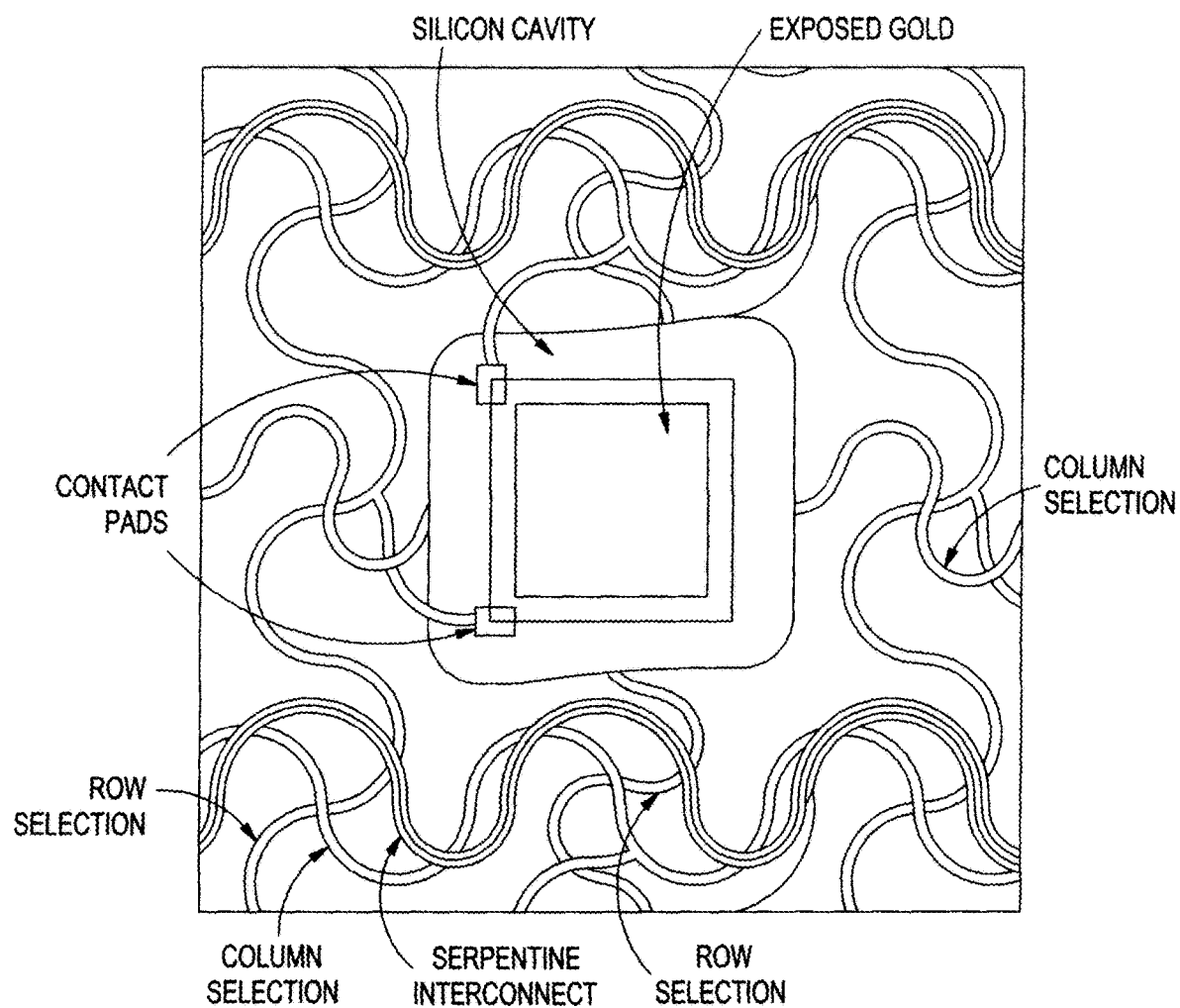
FIG. 1D is an image of one unit of the stacked arrays. Arrows and text in blue, orange and green correspond to layers for electrodes, temperature sensors and pressure sensors, respectively. Scale bar, 200 μm.
Figure 1E:
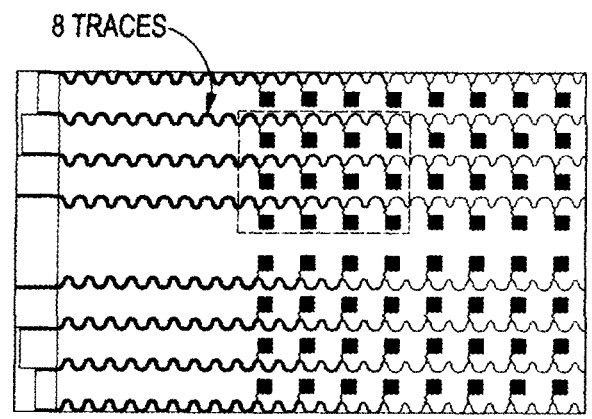
FIG. 1E is an image of the array of electrodes in planar format. Scale bars, 2 mm for the image in the black square, 500 μm for images in the blue dashed outline, and 100 μm for images in the orange dashed outline.
Figure 1E:
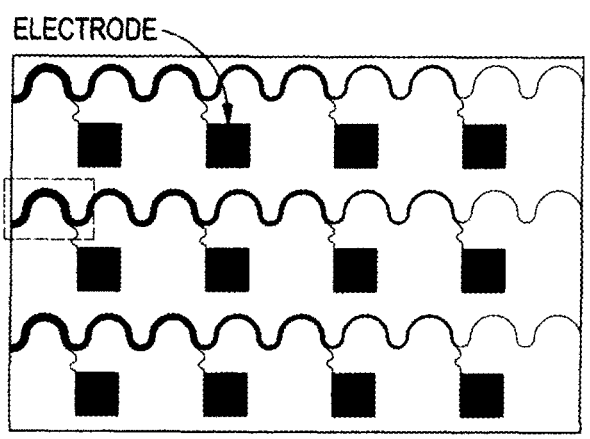
Figure 1E:
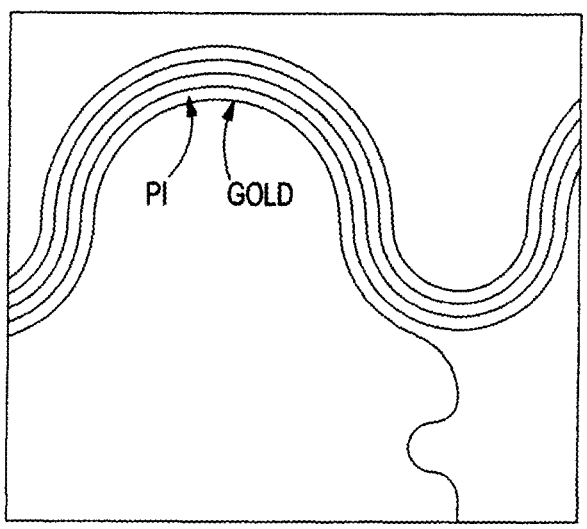
Figure 1F:
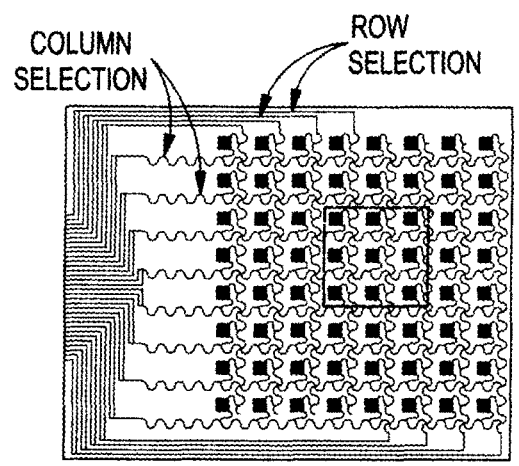
FIG. 1F is an image of the array of electrodes and array of temperature sensors in planar format. Scale bars, 2 mm for the images in the black square, 500 μm for images in the blue outline, and 100 μm for images in the orange dashed outline.
Figure 1F:
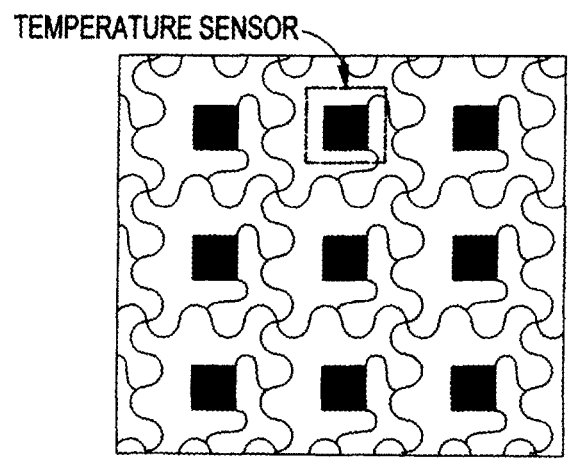
Figure 1F:
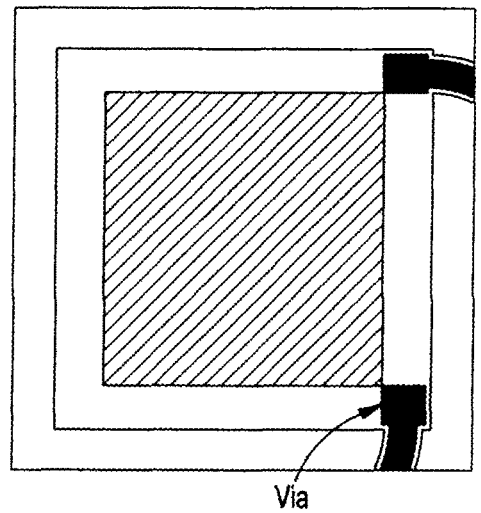
Figure 1G:
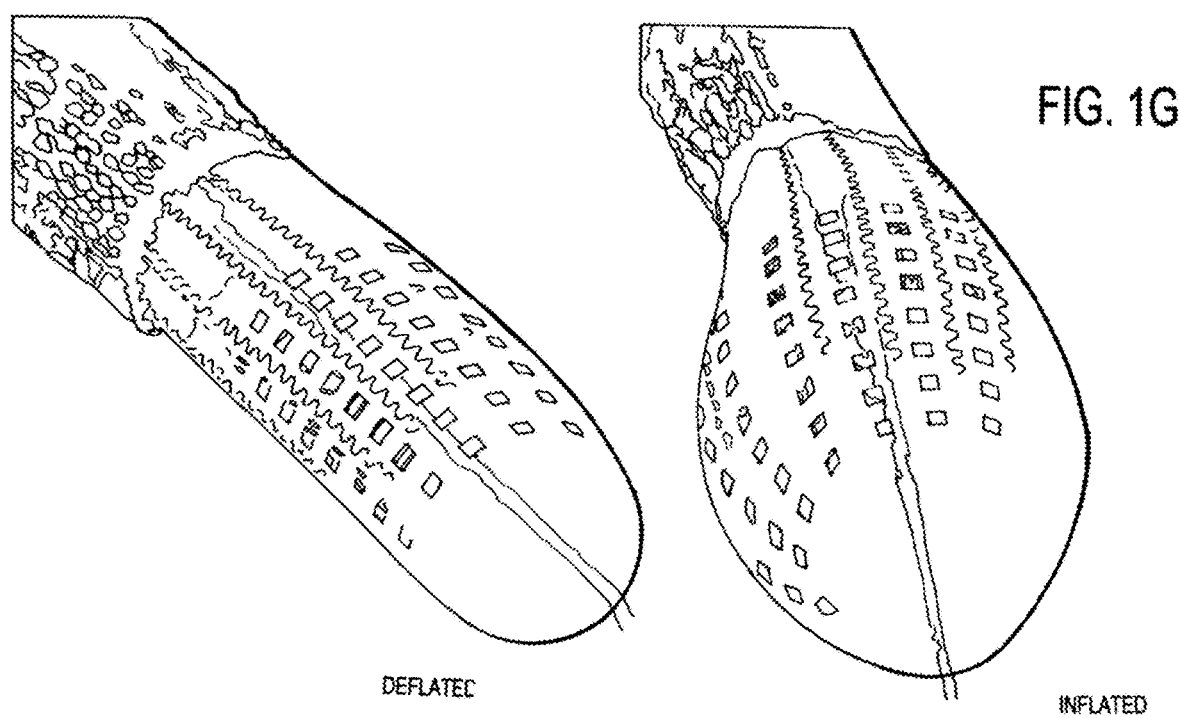
FIG. 1G is an image of the array of electrodes transferred onto a balloon catheter of silicone, shown in a deflated and inflated configuration. Scale bars, 2 mm.
Figure 1H:
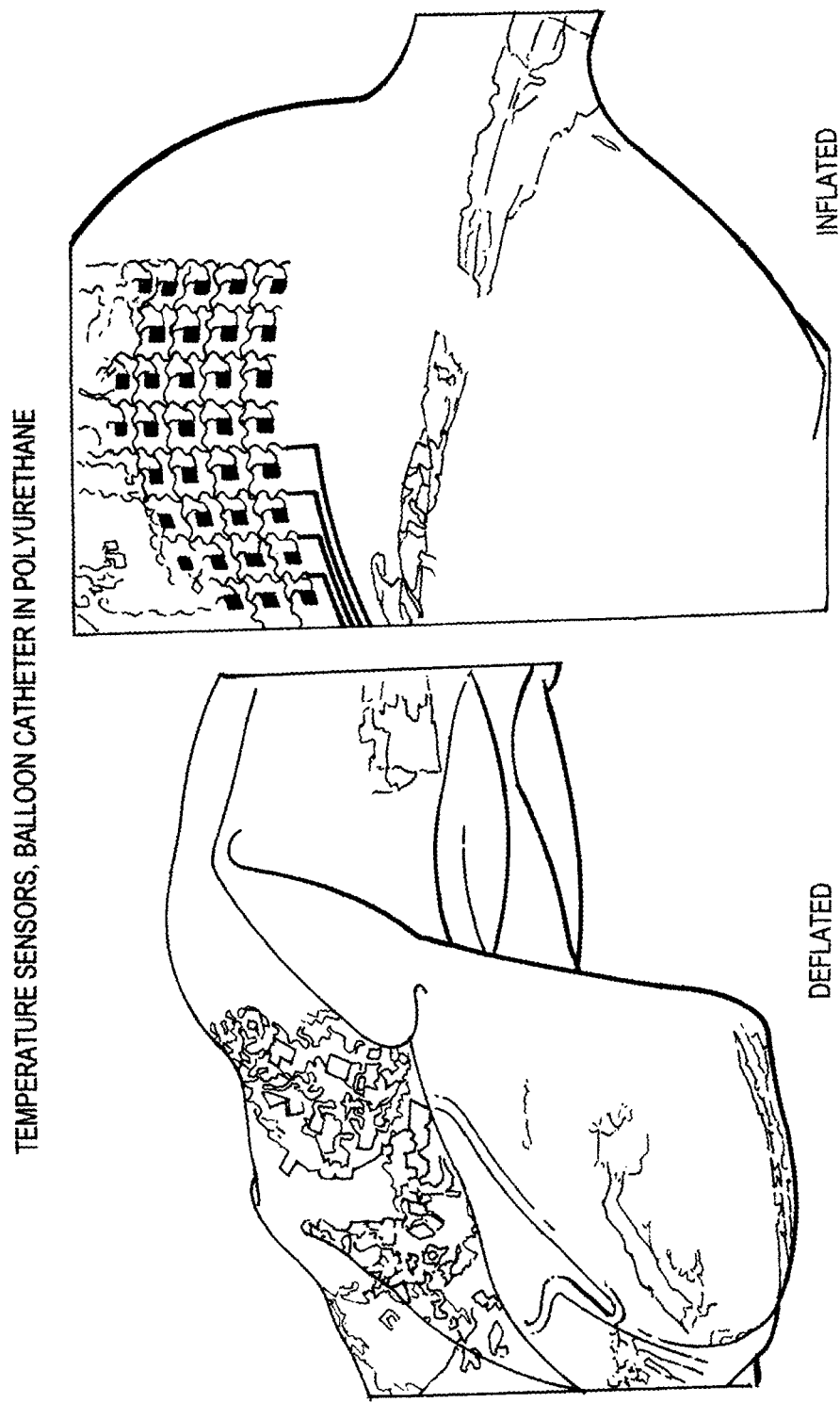
FIG. 1H is an image of the array of temperature sensors transferred on a balloon catheter of polyurethane, shown in a deflated and inflated configuration. Scale bars, 2 mm.

FIG. 1B is an image of an inflated, instrumented balloon catheter inserted into a transparent heart model, where the green dashed curve illustrates the path of the catheter. As shown, the balloon catheter travels from the proximal end of the right atrium to His bundle. FIG. 1C is an image of the vertically stacked arrays of electrodes, temperature sensors and pressure sensors. FIG. 1D is an image of one unit of the stacked arrays. Arrows and text in blue, orange and green correspond to layers for electrodes, temperature sensors and pressure sensors, respectively. FIG. 1E is an image of the array of electrodes in planar format. FIG. 1F is an image of the array of electrodes and array of temperature sensors in planar format.

Precise multi parametric measurements, effective treatments and optimal mechanics (that is, elastic response to compression during deflation and stretching during inflation of the balloon) require careful axial orientation of each layer of sensors and actuators. In this multilayered configuration, the electrode arrays reside on the topmost surface to enable direct contact with biological tissues. Temperature sensors lie subjacent to the electrodes, separated by a thin insulating layer of PI (~6 μm in thickness), to allow tracking of changes in temperature associated with ablation or other procedures. The layer with pressure sensors is located at the bottom, for measurements of the local transverse forces at the interface between the electrodes and the contacting soft tissues.

The vertical stack of arrays of electrodes, temperature sensors and pressure sensors joins the sensing units together as the nodes of the multi layer mesh (positioning and overlay accuracy better than 100 μm across the whole array), but leaves the stretchable interconnects untethered to the elastomeric substrate to enable out-of-plane deformations for enhanced stretchability (>30% of biaxial stretch).

The electrode array consists of exposed Au pads (500 μm×500 μm in lateral dimension, 300 nm in thickness) interconnected by serpentine traces and sandwiched between two layers of PI (3.3 μm in thickness each). These traces adopt optimal geometric designs (Au: 15 μm in width; PI: 21 μm in width) to accommodate biaxial stretching of 30% without inducing fractures in the constituent materials. A multiplexed data-acquisition system includes an application-specific integrated circuit (ASIC) chip (RHD2164, Intan Technologies) to amplify, digitize and multiplex the signals, thereby reducing the total number of wires that connect to the testing instrument from 64 to 8. Using the ASIC chip eliminates the requirement for flexible transistors at each unit cell and enables the system to leverage state-of-the-art microelectronic elements.

Pressure Sensing from Arrays of 3D Mesostructures

For mounting on balloon catheters, these pressure sensor arrays must be not only stretchable, but also robust in response to the extreme mechanical perturbations associated with catheter deployment and navigation through a sheath. Covering the 3D tent-like mesostructures with silicon cavities protects the pressure sensors from various forces associated with these procedures, with additional design flexibility to control their sensitivity. The stretchable features allow the pressure sensor array to conformally integrate with balloons and other soft curvilinear surfaces. Integrating the pressure sensor array onto a customized balloon catheter allows the system to be inserted through small openings with the balloon in its deflated state for spatiotemporal mapping of pressure generated once the inflated balloon makes contact with a target surface.

Electrogram Measurements

The vertically stacked arrays of electrodes and pressure sensors enable synchronized multimodal measurements of electrograms and pressure. Placing the electrode array on the endocardial surface of cardiac tissue yields electrograms and the ability to detect ventricular excitation and repolarization wavefronts.

Multiplexed Data Acquisition and Signal Processing

In one exemplary embodiment of the technology, for electrogram mapping, anisotropic conductive film and laser-defined flexible printed circuit board (PCB) connectors connect the electrode array to a zero insertion force connector soldered to a customized PCB board. The PCB board connects to the Intan 1024ch recording controller through two 36-pin wire adapters, a 64-channel amplifier board (RHD2164), and a serial peripheral interface cable. A commercial software interface simultaneously records electrograms from 64 channels at a sampling rate of 20 kS/s. The bandwidth of the amplifier hardware extend from 0.1 to 200 Hz. A notch filter at 60 Hz further reduces the noise signal from electrical wires. For temperature and pressure mapping, an anisotropic conductive film cable and laser-defined flexible PCB connectors connect the arrays of temperature and pressure sensors to a customized PCB board. Wires from the PCB board join the sensors to a customized circuit for time-division multiplexing. A PowerLab computer interface (ADInstruments, Model 8/35) record the signal from the common path at a sampling rate of 200 kS/s. A square wave at 5 kHz, generated from the PowerLab computer interface, serves as the clock signal for multiplexing. A customized MATLAB code decodes the signal from one common path into 64 traces of signals that correspond with the 64 individual sensors, as shown in FIG. 1C. A digital moving-mean filter with a window size of 20 smoothes the 64 demultiplexed signals.

Advances from the present technology involve (1) the capabilities in high-density multifunctional mapping using devices that adopt both 2D and 3D designs, (2) multilayer, modular layouts that provide scalable paths to technologies with customizable diagnostic and therapeutic functions, and (3) the simultaneous, multimodal operation of arrays of sensors and actuators, with potential for closed-loop control. These features promise to enable physicians to acquire a rich set of physiological information and to complete surgeries in shorter times with a single instrumented-catheter system. The integration strategy can apply to other surgical instruments relevant to procedures on various parts of the nervous system, urinary system, gastrointestinal tract and elsewhere.

Figure 2:
FIG. 2 is a flow diagram showing an exemplary method of operation of an electrical sensing and pacing device in accordance with the present technology.

FIG. 2 is a flow diagram showing an exemplary method of operation of an electrical sensing and pacing device in accordance with the present technology. The method commences at step 202, where the deflated balloon catheter is inserted through the right atrium of a heart. The balloon is equipped with a functional system of multimodal and multiplexed soft sensor arrays (i.e. pressure, temperature, and electrode arrays) to properly guide the catheter to the right atrium. That is in contrast to traditional deflated balloon catheters, which are inserted percutaneously and guided up to the heart and into the right atrium with a guide wire. At step 204, the catheter of the device locates the His bundle region of the heart, using the foregoing system of multimodal and multiplexed soft sensor arrays. The tip of the catheter is preferably positioned at the general location of the His bundle, adjacent to the annulus of the tricuspid valve.

At step 206, the balloon catheter is inflated at the appropriate location and effective contact with the surrounding is tissue is confirmed. Appropriate contact between the pressure sensor and cardiac tissue is required for high-fidelity mapping of electrophysiological signals. Here, pressure sensors are integrated within the device, with each strain gauge designed with a cross-shaped geometry so that small forces can be measured at the soft-tissue interfaces. Additionally, the stretchable features of the pressure sensor array allow it to be conformally integrated onto a balloon catheter that can be inflated or deflated without compromising the integrity of the sensors.

At step 208, the device performs spatiotemporal mapping of His bundle. In performing mapping, the electrode array records electrical His bundle activation in real time with high spatial and temporal resolution, preferably sampled at 1-10 k kS/s and 200-500 μm interelectrode distance. Voltage maps will be created with computer software to illustrate excitation waves as they propagate across the tissue. At step 210, the device locates regions that require electrical stimulation for clinical pacing via real-time electrical mapping. Based on the spatial and temporal voltage maps and recorded electrograms, the investigator will be able to identify the specific area of AV node conduction pathway where the inflated balloon is located. A pace-mapping approach (i.e., stimulating individual electrodes to produce activation pathways originating from different pacing sites and measure pacing thresholds at these different locations) is used to interrogate various tissue regions around the His bundle with programmed stimulation at numerous locations to map electrical excitability and engage either the fast or slow pathway of the AV node and corresponding structures in the His bundle by examining the morphology of QRS complex.

At step 212, the device identifies the minimum pacing threshold for sufficient capture of the His bundle and Purkinje fibers by identifying appropriate electromechanical stimulation of the ventricular tissue During the pace-mapping procedure, pacing capabilities of individual electrode arrays are tested at different areas to determine the number of electrodes and lowest pacing thresholds necessary for sufficient capture for each heart. At step 214, the device guides and implants permanent pacing electrode at the appropriate location based on its spatiotemporal mapping and analysis of steps 208 through 12. Implantation is optimally positioned for appropriate s-HBP or ns-HBP for the particular heart.

Figure 3:
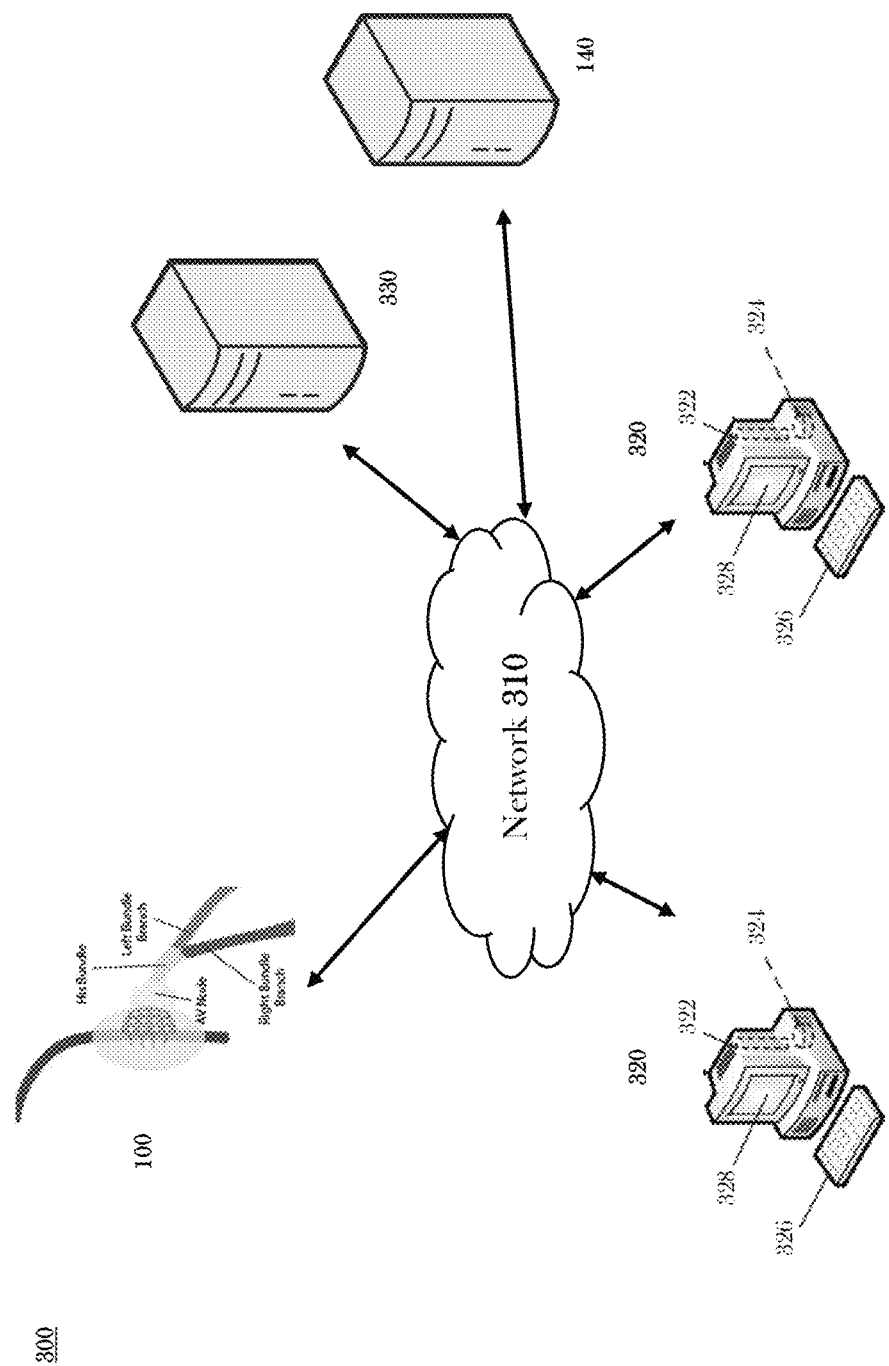
FIG. 3 is an exemplary embodiment of the hardware of the electrical sensing and pacing system.

FIG. 3 is an exemplary embodiment of the hardware of the electrical sensing system. In the exemplary system 300, one or more electrical sensing and pacing devices 100 are connected to one or more computers 320 through a network 310. In certain embodiments, the computers 320 may also connect to the electrical sensing and pacing devices 200 through a wired connection. The network 310 may be a wide-area network, like the Internet, or a local area network, like an intranet. Because of the network 310, the physical location of the electrical sensing and pacing devices 100 and the computers 320 has no effect on the functionality of the hardware or software of the invention. Both implementations are described herein, and unless specified, it is contemplated that the electrical sensing and pacing devices 100 and the computers 320 may be in the same or in different physical locations. Communication between the hardware of the system may be accomplished in numerous known ways, for example using network connectivity components such as a modem or Ethernet adapter. The electrical sensing and pacing devices 100 and the computers 320 will both include or be attached to communication equipment. Communications are contemplated as occurring through industry-standard protocols such as HTTP or HTTPS.

Each computer 320 is comprised of a central processing unit 322, a storage medium 324, a user-input device 326, and a display 328. Examples of computers that may be used are: commercially available personal computers, open source computing devices (e.g. Raspberry Pi), commercially available servers, and commercially available portable devices (e.g. smartphones, smartwatches, tablets). In one embodiment, each of the electrical sensing and pacing devices 100 and each of the computers 320 of the system may have software related to the system installed on it. In such an embodiment, system data may be stored locally on the networked computers 320 or alternately, on one or more remote servers 330 that are accessible to any of the electrical sensing and pacing devices 100 or the networked computers 320 through a network 310. In alternate embodiments, the software may run as an application on the electrical sensing and pacing devices 100. In certain embodiments, the computers 320 determine and apply stimulation, as square waves of bipolar stimulation at a range of frequencies are generated from the computer interface, preferably a PowerLab interface. The computers 320 also analyze the sensed data from the electrical sensing and pacing device 100, preferably using custom MATLAB software and the PFEIFER GUI. Electrograms may be then recorded on a PowerLab computer interface and analyzed with software such as LabChart.

Figure 4:
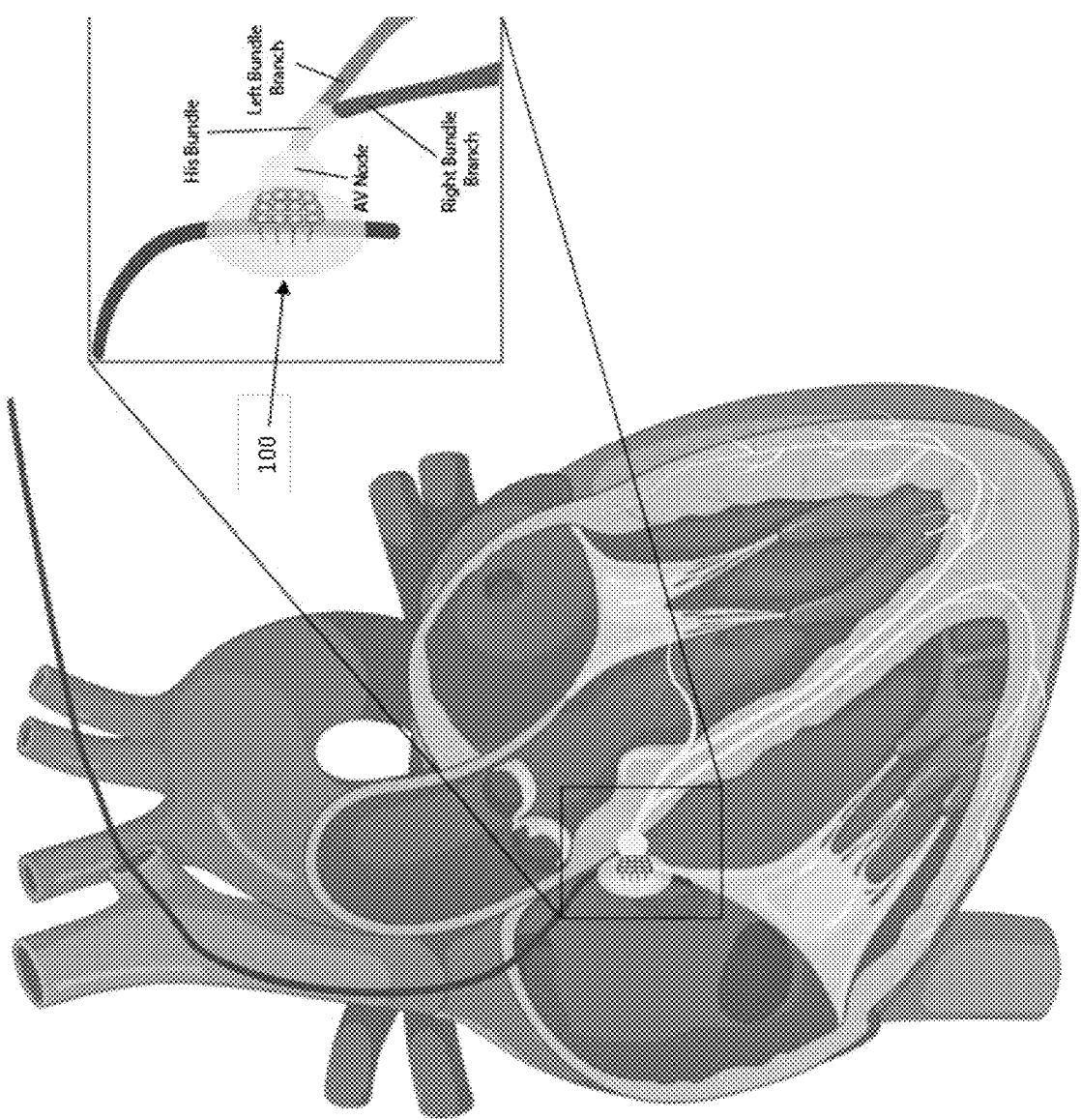
FIG. 4 is a diagram of the multimodal, multilayered soft electronics in advanced devices intended for cardiac surgery, shown in relation to their operation in a heart.

The present technology comprises multimodal, multilayered soft electronics in advanced devices 100 intended for cardiac surgery, as exemplarily shown in FIG. 4. Specifically, these advanced classes of medical instruments 100 enable soft contacts conformal to curved tissue surfaces—such as the His bundle area—with the ability to navigate in spatially restrictive locations via minimally invasive techniques. As seen in FIG. 4, the most recent class of soft electronics 100 can be integrated onto a balloon catheter with multiplexed arrays of stretchable interconnects for multifunctional spatiotemporal mapping as well as spatially defined electrical stimulation, all while leveraging fast switching and multiplexing capabilities across rows and columns of elements. These devices offer multifunctional capabilities, including electrophysiological mapping and pacing, force of contact mapping, temperature mapping, and radiofrequency (RF) and irreversible electroporation (IRE) ablation. All these capabilities offer the unique opportunity to (1) navigate a novel state-of-the-art balloon catheter to approximately a 1 $cm^2$ area targeted for His bundle pacing, (2) establish firm contact across the array ensured by contact force mapping, (3) provide electrical potential mapping and optical mapping data during programmed S1S2(S3) stimulation from the atrium or ventricle, (4) provide pace-mapping pacing threshold data during pacing from each electrodes (one at a time) located over the His bundle and mapping from the remaining electrodes and optical mapping, and (5) identify the optimal area of His bundle pacing for implanting a permanent lead and ablating the AV node using IRE to capture the His bundle after AV node ablation.

Figure 5A:
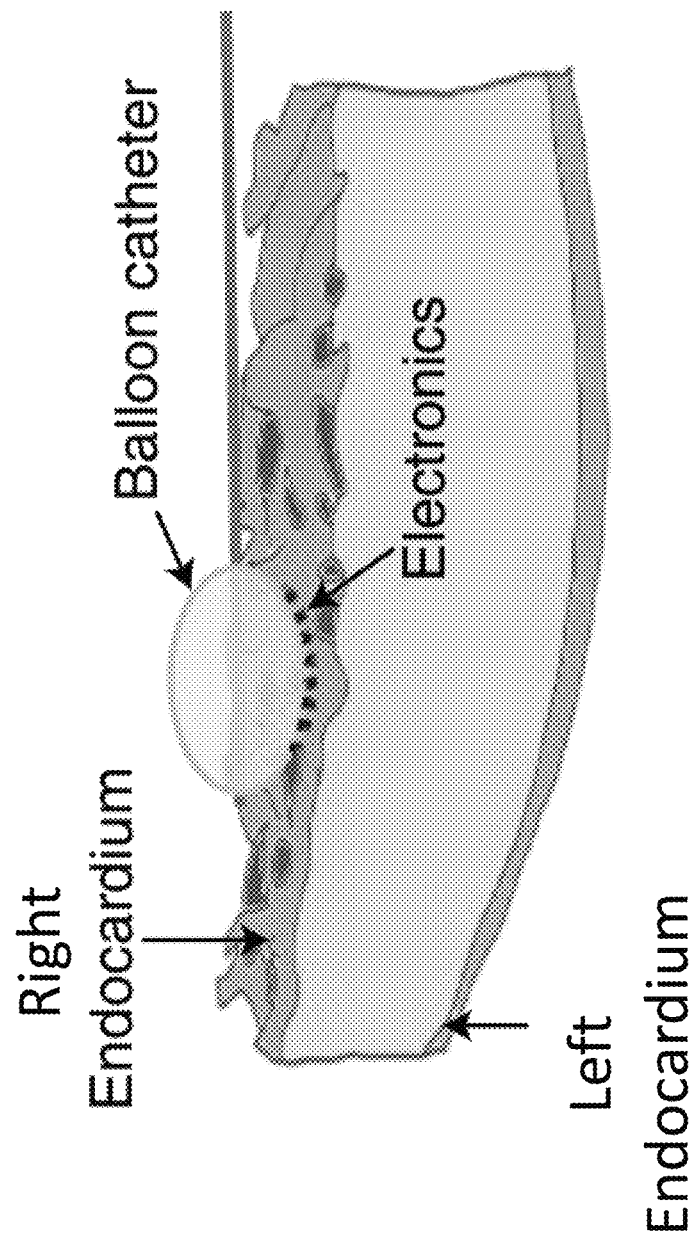
FIG. 5A is a diagram showing an exemplary embodiment of the electrical sensing and pacing system set up for real-time electrical mapping.
Figure 5B:
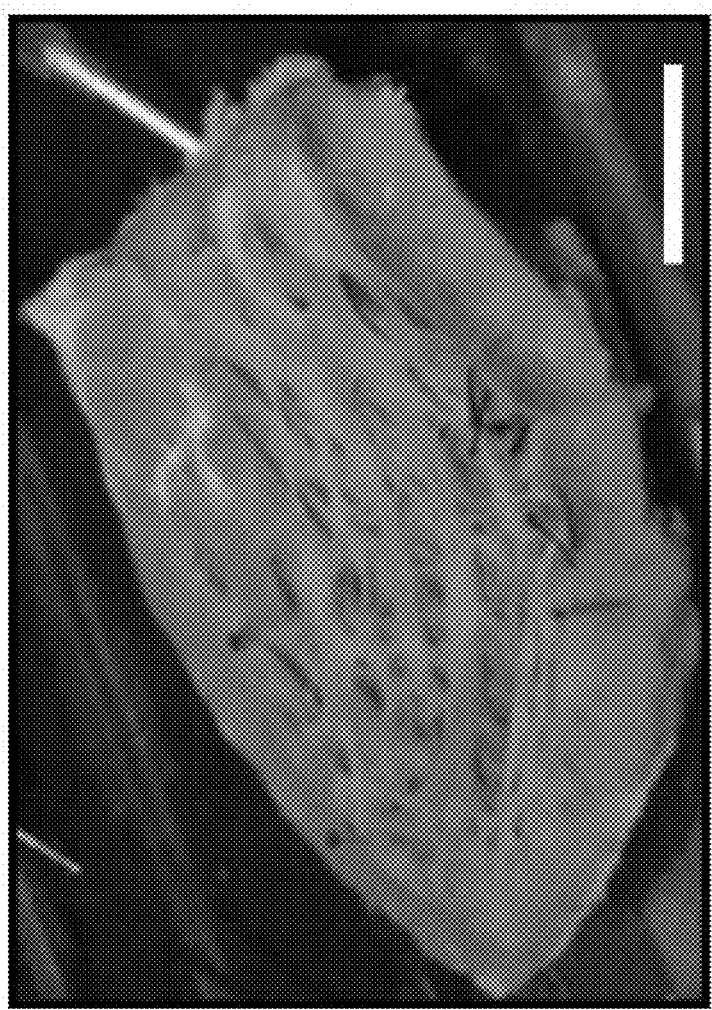
FIG. 5B is an exemplary image of the endocardial surface of a human ventricle. Scale bar, 15 mm.

FIG. 5A is a diagram showing an exemplary embodiment of the electrical sensing and pacing system set up for real-time electrical mapping. As shown, the balloon catheter is inserted into heart tissue. The balloon catheters surface is comprised of the electronics of the electrical sensing and pacing system, which include vertically stacked arrays of electrodes, temperature sensors and pressure sensors. Placing electrode array on the endocardial surface of cardiac tissue allows the system to compile electrograms detect ventricular excitation and repolarization wavefronts. Similarly, the temperature sensors of the system allow tracking of changes in temperature associated with ablation or other procedures conducted by the system, while the pressure sensors perform measurements of the local transverse forces at the interface between the electrodes and the contacting soft tissues, which include the right endocardium and left endocardium. FIG. 5B is an exemplary image of the endocardial surface of a human ventricle, showing the right endocardium and left endocardium in human cardiac tissue.

Figure 5C:
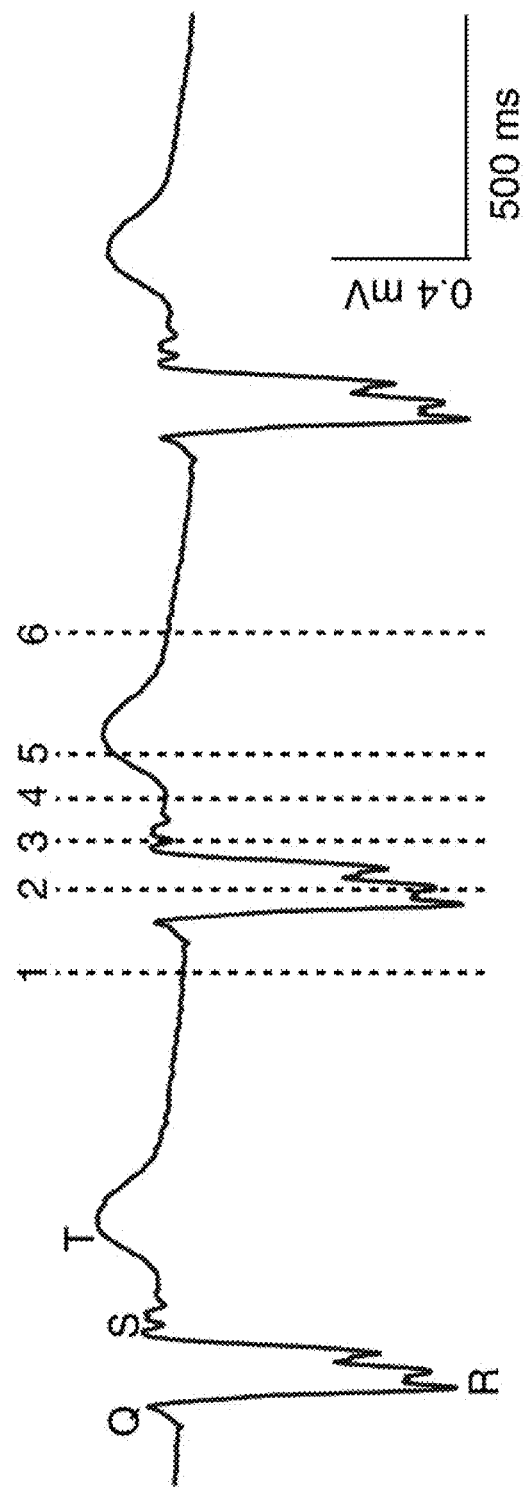
FIG. 5C is an exemplary single trace electrogram as measured from the electrode array of the electrical sensing and pacing system under electrical pacing at 60 beats per minute.
Figure 5D:
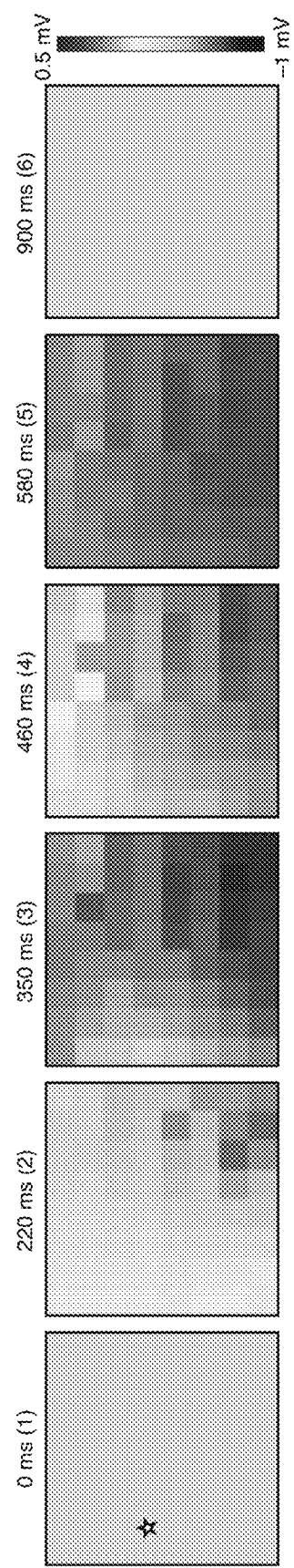
FIG. 5D shows exemplary spatial and temporal voltage maps at different time points (1) through (6), as indicated by the black dashed lines in FIG. 5C. The star indicates the pixel that corresponds to the trace in FIG. 5C.

FIG. 5C is an exemplary single trace electrogram as measured from the electrode array of the electrical sensing and pacing system under electrical pacing at 60 beats per minute. FIG. 5C shows the Q, R, S and T waves associated with electrical impulses in cardiac tissue. Placing the electrode array on the endocardial surface of the left ventricle, as shown in FIGS. 5A and 5B, yields electrograms and the ability to detect ventricular excitation and repolarization wavefronts, as shown in FIG. 5C. The numbers (1), (2), (3), (4), (5), and (6) represent different time points in the electrogram. FIG. 5D shows exemplary spatial and temporal voltage maps at different time points (1) through (6), as indicated by the black dashed lines in FIG. 5C, to highlight sensing of the excitation wave (time points (2) and (3)) and the repolarization wave (time point (5)) propagating along the endocardial surface. The star indicates the pixel that corresponds to the trace in FIG. 5C.

Figures 5E, 5F:
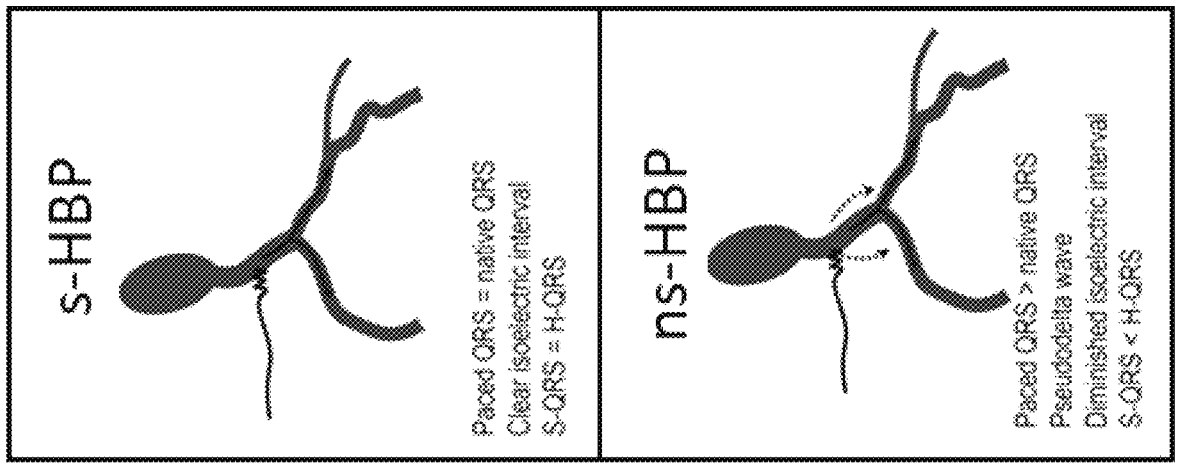
FIG. 5E is a schematic diagram of selective His bundle pacing (s-HBP), which can be confirmed when the time interval between the stimulus and initiation of the QRS complex (s-QRS) is equal to the time interval between the His electrogram and the ORS complex (H-QRS).
FIG. 5F is a schematic diagram of non-selective His bundle pacing (ns-HBP), which can be confirmed when the time interval between the stimulus and initiation of the QRS complex (s-QRS) is less than the time interval between the His electrogram and the QRS complex (H-QRS).

FIGS. 5E and 5F are schematic diagrams showing selective and non-selective His bundle pacing, which the system is able to record and detect. FIG. 5E is a schematic diagram of selective His bundle pacing (s-HBP), where there is ventricular activation solely over the His-Purkinje system, and which can be confirmed when the time interval between the stimulus and initiation of the QRS complex (s-QRS) is equal to the time interval between the His electrogram and the QRS complex (H-QRS). By contrast, FIG. 5F is a schematic diagram of non-selective His bundle pacing (ns-HBP), which can be confirmed when the time interval between the stimulus and initiation of the QRS complex (s-QRS) is less than the time interval between the His electrogram and the QRS complex (H-QRS).

The present technology improves the recent designs of multimodal soft electronics in a novel conformal bioelectronic catheter, exemplarily toward the goal of navigating and implanting s-HBP in the human heart. The novel catheter will allow precise electrical mapping the area of His bundle above and below the valves from both the right and left septum; it will systematically map selective and non-selective His excitation thresholds across the mapping area, while dual-side optical mapping will assess 3D conduction patterns and longitudinal dissociation within the AV node and His bundle at different pacing strengths. Anatomic location will be mapped using electrograms recorded by the array during anterograde and retrograde pacing, applied to atrial and ventricular tissue, respectively. His bundle will be located based on presence of His bundle electrogram after atrial or ventricular complexes, respectively. A machine learning algorithm is used to automate detection of His bundle electrogram in electrodes located at the anatomical sites of His bundle using iterative learning from prior mappings. The machine learning algorithm acquires, filters, and displays electrical signals with high spatial and temporal resolution for real-time mapping of the spread of electrical activation. The process of pace-mapping involves iterative pacing of each of the electrodes at different stimulus voltages to elicit capture of the His bundle. Confirmation of s-HBP or ns-HBP is determined as described above, with regard to FIGS. 5A-5F. Then, using the known location of the His bundle, electrodes of the system are used for pace-mapping to measure threshold of excitation of selective and non-selective His bundle pacing. Pacing stimuli of increasing strength is applied from electrodes located at the His bundle (one at a time) and electrograms will be recorded by the rest of the multielectrode matrix. The machine learning algorithm is used to detect selective excitation of the His bundle (sHBP) without excitation of nearby ventricular myocardium versus non-selective His bundle pacing (nsHBP). Delta-shaped morphologies of global QRS complexes serves as the evidence for nsHBP. Anatomical map of thresholds of sHBP and nsHBP are used to determine an optimal site for subsequent permanent implantation site for sHBP or nsHBP.

Example 1

Methodology

The novel conformal bioelectronics catheter is custom designed to enable precise implantation of a s-HBP lead into human patients with precision currently unattainable with available HBP techniques, where pacing leads are implanted via venous access and a sheath is advanced over a guidewire for lead advancement toward the tip of the sheath. However, instead of a single unipolar pacing lead anchoring into the hearts endocardium with screwing mechanisms, this device innovatively employs an expandable and stretchable catheter with soft surface conformal electronics at the tip of the sheath to allow for detailed pace-mapping of the His bundle area to identify the ideal location of a permanent pacing lead, which are inserted via the balloon catheter and affixed at the optimal pacing location. Electrode arrays are situated against the tissue of interest with guidance from the devices pressure sensor arrays, and electrodes will be capable of both sensing (for real-time in vivo mapping) and pacing (for real-time in vivo stimulation). A clinical protocol will be developed for automated mapping of the His pacing threshold for s-HBP from the balloon multilayered catheter. Following identification of the optimal site of pacing, a clinical His pacing lead are implanted for s-HBP and tested. Novel designs of s-HBP leads which are not based on the potentially damaging screw design are also contemplated as within the scope of this technology.

Data Collection and Analysis

Multilayered surface conformal electrode arrays are tested on ex vivo donor human hearts. Sensing capabilities of the devices are tested at the site of the AV node junction and correlated to simultaneous optical maps derived from either the same side of the tissue preparation or the opposing side of the septal region. The electrical and optical signals are collected as the amplified voltage or photovoltage and analyzed via MATLAB-based RHYTHM software developed in our laboratory. Pacing capabilities of the electrode arrays are tested at different areas to determine the number of electrodes and lowest pacing thresholds necessary for sufficient capture (i.e., pace-mapping). Signals and patterns recorded during steady state pacing will serve as the baseline. Signals and patterns recorded during S1S2 pacing are statistically compared with the baseline data. Data are expressed as means±SEM. Independent t tests, one- or two-way ANOVA followed by Bonferroni posttests, MATLAB (version R2016b), and Graph Pad Prism 6 are used for all data analysis, computation, and statistical comparisons. P values <0.05 are defined as significant. Detailed statistical design and implementation are presented in our recent publications. Based on these analyses, the device maps the Hs bundle and optimally guides implantation of the s-HBP or ns-HBP lead.

The balloon catheter with soft electronics can simultaneously sense and pace electrical activity of the His bundle in the human heart, which also has pressure-sensing capabilities for establishing optimal contact with the endocardium. This device improves clinical HBP for the myriad patients who could benefit from such conduction system pacing, and for whom are not capable of receiving RV pacing or CRT to relieve their symptoms.

The foregoing description and drawings should be considered as illustrative only of the principles of the invention. The invention is not intended to be limited by the preferred embodiment and may be implemented in a variety of ways that will be clear to one of ordinary skill in the art. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. An electrical sensing and pacing device comprising:
    a balloon catheter;
    a first layer connected to or embedded in said balloon catheter, said first layer having an electrode array with a plurality of electrodes configured to or adapted to be positioned on the atrioventricular junction or His bundle anatomical area, wherein the electrode array determines electrical His bundle activation with high spatial and temporal resolution, said first layer having a first top polymer film layer with openings, the plurality of electrodes positioned in the openings, and a first bottom polymer film layer; and
    a second layer connected to or embedded in said balloon catheter, said second layer having a pressure sensor array with a plurality of pressure sensors, said second layer having a second silicon layer with cavities, the plurality of pressure sensors positioned in the cavities, and a second bottom polymer film layer.

2. The electrical sensing and pacing device of claim 1, wherein the balloon catheter, the first layer, and the second layer are bendable and stretchable.

3. The electrical sensing and pacing device of claim 1, wherein the electrode array records electrical His bundle activation.

4. The electrical sensing and pacing device of claim 1, wherein the electrode array paces electrical His bundle activation.

5. The electrical sensing and pacing device of claim 1, further comprising a separate bendable and stretchable third layer connected to or embedded in said balloon catheter, said third layer separate from said first layer and said second layer and having a temperature sensor array with a plurality of temperature sensors, a third top polymer layer, a third bottom polymer layer, and the plurality of temperature sensors positioned between the third top polymer layer and the third bottom polymer layer.

6. The electrical sensing and pacing device of claim 1, wherein the electrode array therapeutically ablates tissue of the atrioventricular junction or the His bundle anatomical area.

7. The electrical sensing and pacing device of claim 1, wherein the electrode array identifies selective His bundle stimulation and non-selective His bundle stimulation.

8. The electrical sensing and pacing device of claim 1, wherein said second layer is multimodal, multiplexed soft electronics.

9. The electrical sensing and pacing device of claim 1, wherein said balloon catheter comprises a polymer.

10. The electrical sensing and pacing device of claim 1, wherein said first layer and said second layer each comprise stretchable interconnects to form a multiplexed array.

11. The electrical sensing and pacing device of claim 1, wherein said electrode array makes electrophysiological recordings and applies electrical stimulation.

12. The electrical sensing and pacing device of claim 1, wherein said pressure sensor array measures forces associated with soft tissue contact.

13. The electrical sensing and pacing device of claim 1, wherein said electrical sensing and pacing device maps a His bundle region.

14. The electrical sensing and pacing device of claim 1, wherein said balloon catheter has a deflated configuration whereby said electrical sensing and pacing device is configured to or adapted to be inserted to a His bundle region, and an inflated configuration that presses said electrode array onto the His bundle region.

15. The electrical sensing and pacing device of claim 1, whereby said pressure sensor array measures tissue contact.

16. The electrical sensing and pacing device of claim 1, further comprising a processing device in communication with said electrode array to perform multifunctional spatiotemporal mapping of a human heart's intrinsic electrical activity or with pacing from the atrial or ventricular myocardium.

17. The electrical sensing and pacing device of claim 1, further comprising a processing device measuring and locating an optimal pacing site.

18. The electrical sensing and pacing device of claim 1, further comprising a processing device in communication with said electrode array and controlling each of said plurality of electrodes to selectively and individually stimulate tissue area beneath that electrode, said processing device receiving signals from said plurality of electrodes to identify a type of conduction block.

19. The electrical sensing and pacing device of claim 18, said processing device observing a functional response of each of said plurality of electrodes to evaluate pacing.

20. The electrical sensing and pacing device of claim 18, said processing device determining a clinically optimal placement for permanent implantation of an electrical pacing device.

21. The electrical sensing and pacing device of claim 18, said processing device determining a minimum pacing threshold for capture of either the cardiac conduction system or myocardial tissue.

22. The electrical sensing and pacing device of claim 1, further comprising a second top polymer film layer positioned between the second silicon layer and the second bottom polymer film layer.

* * * * *